US00PP09412P

United States Patent [19]

Schumann

[11] Patent Number: Plant 9,412

[45] Date of Patent: Dec. 26, 1995

[54] GERANIUM PLANT NAMED FISGETI

[75] Inventor: Ingeborg Schumann, Albstadt, Germany

[73] Assignee: Florfis AG, Binningen, Switzerland

[21] Appl. No.: 360,342

[22] Filed: Dec. 21, 1994

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Foley & Lardner

[57] ABSTRACT

A new and distinct cultivar of geranium plant named Fisgeti, particularly characterized by the combined features of light rose red flower color with a slight bluish tint, medium green foliage with weak zonation, strongly lobed leaves resembling the leaves of maple trees, vigorous but comparatively compact growth habit, very good branching ability, and early flower response.

1 Drawing Sheet

The present invention comprises a new and distinct cultivar of geranium, botanically known as *Pelargonium peltatum* l'Hert, commonly referred to as ivy geranium, and referred to by the cultivar name Fisgeti.

Fisgeti is a product of planned breeding program which had the objective of creating new ivy geranium cultivars with pink flower color and vigorous but well-branched growth habit.

Fisgeti was originated from a hybridization made by inventor Ingeborg Schumann in a controlled breeding program in Galdar, Gran Canaria, Spain in 1987. The female parent was the cultivar M. J. Cole, having bluish pink semi-double flowers, compact plant habit, and early flower response. The male parent was Salmon Queen, characterized by its salmon pink semi-double flowers, compact plant habit and early flower response.

Fisgeti was discovered and selected as one flowering plant within the progeny of the stated cross by Ingeborg Schumann in 1988 in a controlled environment in Galdar, Gran Canaria, Spain.

The first act of asexual reproduction of Fisgeti was accomplished when vegetative cuttings were taken from the initial selection in autumn 1989 in a controlled environment in Galdar, Gran Canaria, Spain, by, or under the supervision of, Ingeborg Schumann.

Horticultural examination of plants grown from these cutting initiated in May 1990, and continuing thereafter, has demonstrated that the combination of characteristics as herein disclosed for Fisgeti are firmly fixed and are retained through successive generations of asexual reproduction.

Fisgeti has not been observed under all possible environmental conditions. The phenotype may vary significantly with variations in environment such as temperature, light intensity and daylength without, however, any variation in genotype. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Fisgeti, which, in combination, distinguish this geranium as a new and distinct cultivar:

1. Light rose red flower color with a slight bluish tint.
2. Medium green leaves with weak zonation.
3. Vigorous growth habit but comparatively compact.
4. Strongly lobed leaves, resembling the leaves of maple trees.
5. Very good branching ability.
6. Early flower response.

Of the many commercial cultivars known to the present inventors, the most similar in comparison to Fisgeti is the unpatented commercial cultivar Rigi. Reference is made to attached Chart A which compares certain characteristics of Fisgeti to those same characteristics of Rigi. In general comparison to Rigi, Fisgeti has a more intense flower color and a different plant habit. Both cultivars are vigorous growers, but Fisgeti has much better branching. The internodes are shorter in Fisgeti, and the leaf zonation is stronger in Rigi.

The accompanying color photographic drawing shows typical flower and foliage characteristics of Fisgeti, with colors being as true as possible with illustrations of this type.

In the following description, color references are made to The Royal Horticultural Society Colour Chart. The color values were determined indoors in May from plants grown indoors in Hillscheid, Federal Republic of German.

Classification:

*Botanical.*—A hybrid of the species *Pelargonium peltatum* l'Hert.

*Commercial.*—Ivy geranium, cv., Fisgeti.

Inflorescence:

*Umbel.*—Shape: Semi-spherical. Average diameter: 85 mm. Average depth: 50 mm. Peduncle length: 150 mm. Pedicel length: 24 mm. Pedicel color: Green, upper part red. Number of flowers per umbel: 12–15.

*Corolla.*—Average diameter: 50 mm. Form: Semi-double. Number of petals: 8–9. Number of petaloids: 1. Color (general tonality from a distance of three meters): Light rose red to carmine Color of upper petals: 57B–58B. Color of lower petals: 57C. Markings on upper petals:: Dark red veins and a white or light pink stripe between veins. Color of lower surface of petals: 55A and lighter. Color of sepals: Green; largest sepal has anthocyanin coloring. Number of sepals: 5–6.

*Bud.*—Shape: Narrow, elliptical. Color (adaxial): Medium green. Color (abaxial): Red and white, marbled.

*Reproductive organs.*— Androecium: 7 fertile anthers, white filaments, orange-yellow pollen. Gynoecium: 5–6 lobed stigma, white style and pink stigma.

*Spring flowering response period.*—In Hillscheid, Federal Republic of Germany, in 1993 plants had on average 2.5 flowers opened 15 weeks after planting of unrooted cuttings.

*Outdoor flower production.*—The flower count in 1993 in Hillscheid, Federal Republic of Germany was between 75 and 80 flowers per plant for May through September observation period.

*Durability.*—Shatter resistance good.

Plant:

*Foliage.*—Form: Ivy-shaped with strong lobes. Margin: Entire, apart from notches near the tips of lobes. Size of leaf: 100 mm. Color of upper surface: Medium green, approximately 137C-D. Color (zonation): Olive, approximately 147A. Tolerance of botrytis: Average.

*General appearance and form.*— Internode length: 4.5–5.5 cm. Branching pattern: 4.7 branches per week. Length: 80 cm (in September, 35-week-old plants).

CHART A

| CHARACTERISTIC | FISGETI | RIGI |
|---|---|---|
| Flower color | 57B–58B | 57C |
| Plant length | 75–80 cm | 100 cm |
| Internodes | 45–55 mm | 50–80 mm |
| Zonation | Weak | Strong |

It is claimed:

1. A new and distinct cultivar of geranium plant named Fisgeti, as illustrated and described.

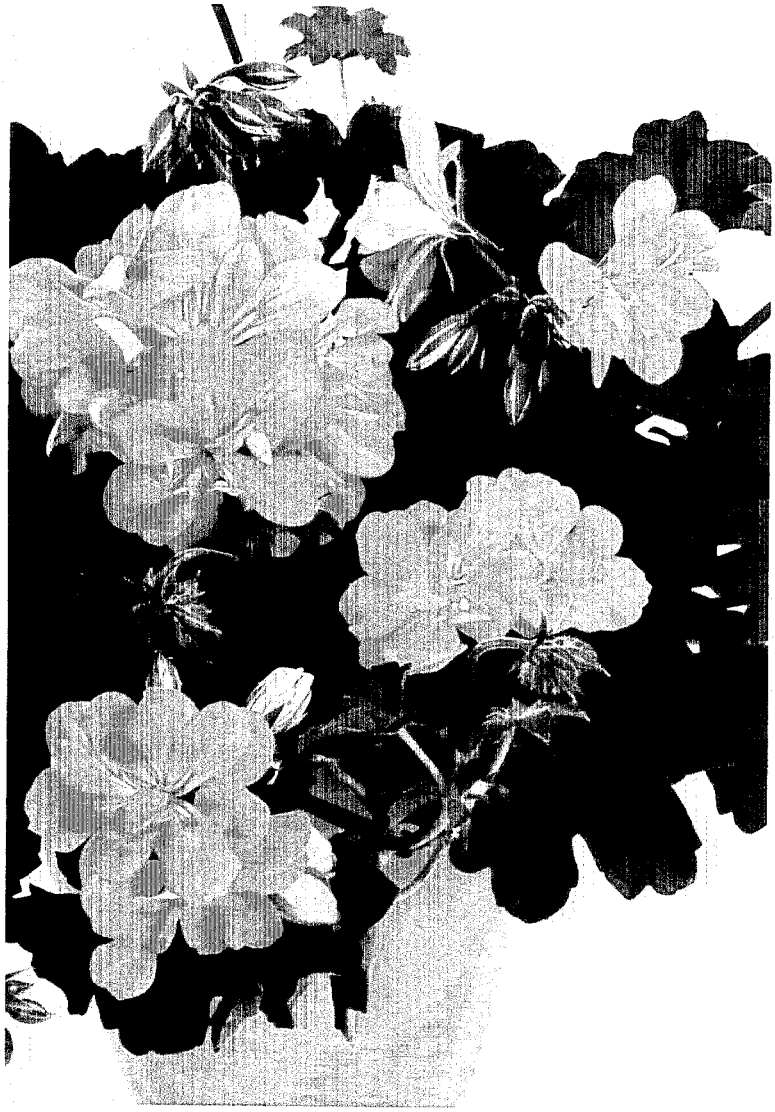

* * * * *